United States Patent [19]
Carbone

[11] Patent Number: 5,116,378
[45] Date of Patent: * May 26, 1992

[54] METHOD AND APPARATUS FOR EXPANDING A SHAFT FOR USE IN PROSTHESIS

[75] Inventor: John J. Carbone, Baltimore, Md.

[73] Assignee: Orthovations, Inc., Baltimore, Md.

[*] Notice: The portion of the term of this patent subsequent to Jul. 16, 2008 has been disclaimed.

[21] Appl. No.: 517,766

[22] Filed: May 2, 1990

Related U.S. Application Data

[63] Continuation-in-part of Ser. No. 468,731, Jan. 23, 1990, Pat. No. 5,032,133.

[51] Int. Cl.$^5$ ............................................. A61F 2/34
[52] U.S. Cl. ............................................ 623/23; 623/18
[58] Field of Search ................. 623/16, 18, 20, 28; 441/75; 606/63, 62, 64

[56] References Cited

U.S. PATENT DOCUMENTS

4,605,350  8/1986  Chater et al. ........................ 411/75

Primary Examiner—David J. Isabella
Attorney, Agent, or Firm—Cushman, Darby & Cushman

[57] ABSTRACT

A prosthetic device includes two or more members having alignable bores and smooth sliding surfaces intercepting the respective bore at an angle; a shaft extending through each bore holds the members in assembled relation with the sliding surfaces abutting one another; rotation of the shaft effects relative sliding motion between the members to vary the width dimension of the device.

16 Claims, 9 Drawing Sheets

METHOD AND APPARATUS FOR EXPANDING A SHAFT FOR USE IN PROSTHESIS

FIELD OF THE INVENTION

This is a continuation of U.S. patent application Ser. No. 07/468,731, filed on Jan. 23, 1990.

The present invention relates to a device for anchoring a prosthetic member in bone structure and, more particularly, to an anchoring device for use in a hip joint prosthesis and which will minimize, if not eliminate, the imposition of unnecessary stresses on the femur while assuring precise positioning of the prosthesis for cooperation with a compatible socket member.

BACKGROUND OF THE INVENTION

Surgical procedures for replacement of a deteriorated or injured hip joint have employed a number of prosthetic devices which have endeavored to address the problems of ease of use, durability of the prosthesis, adjustment thereof, precision in positioning of the prosthesis as well as preservation of as much of the original bone structure as is practical in light of the extent of the development of arthrosis or of an injury that may have occurred.

In one type of arrangement such as that disclosed in U.S. Pat. No. 4,115,875 a tapered and curved shaft is provided for intramedullary positioning in the femur. While this and similar structures have enjoyed widespread use, they suffer from a number of significant disadvantages. Among these, prominent is the difficulty in anchoring the shaft in place. Under conventional procedures, the shaft has typically been forcibly inserted by the practitioner often with the aid of a mallet or similar tool. The type as well as frequency of damage to the femur has greatly contributed to the failure of this type of prosthesis and complication of the surgical procedure. In addition, the durability of the shaft member, once inserted has not been satisfactory due to the tendency of the shaft to become loose and to move relative to the femoral cavity. In addition, removal of the prosthesis for readjustment or replacement is time consuming and difficult for the patient.

Other devices have attempted to solve the anchoring problem but, in general, these solutions have been at the expense of the integrity of the prosthetic implant, have been difficult to set in place or have imposed concentrated stresses along the length of the femoral cavity thereby resulting in potential damage to the femur. In this connection, reference may be had to U.S. Pat. Nos. 3,846,846, 4,520,511 and 4,530,115.

SUMMARY OF THE INVENTION

It is an object of the present invention to provide a method and device for insertion into a bone structure and which can be precisely positioned and anchored in place much more readily than the devices of the prior art and which will avoid imposing dangerous or uncontrollably concentrated stresses on the bone structure. In addition, the present invention will provide a prosthetic device which will greatly facilitate its insertion into a bone cavity as well as subsequent readjustment for positioning purposes. Further, the device of the present invention will be much more durable in use than many of the devices of the prior art.

In a preferred embodiment, the present invention provides a device for intramedullary insertion and anchoring and comprises two members having elongated abutting surfaces permitting relative sliding motion between the two members upon actuation of a locking device which serves to adjust the positions of the two members relative to one another and to lock the two members in a desired position after insertion into a bone cavity. When assembled, the two members will define a shaft structure which, upon relative movement of the two members in one direction will effect anchoring as a result of substantially radial expansion of the shaft in a bone cavity. In another embodiment, the device of the invention is provided with three members with one of these disposed for relative sliding movement between end members which themselves are movable relative to each other. The locking device serves to retain the three members in the assembled condition as well as to cause, upon actuation, radial expansion and locking once inserted into a bone cavity. With each of these arrangements, the stresses normally imposed on the bone as a result of the anchoring operation will be distributed substantially uniformly over the length of the shaft thereby minimizing or eliminating any undesirable concentration of stresses on the adjacent bone structure.

The foregoing and other advantages will become apparent as consideration is given to the following detailed description taken in conjunction with the accompanying drawings, in which:

DETAILED DESCRIPTION OF THE INVENTION

Figure 1:
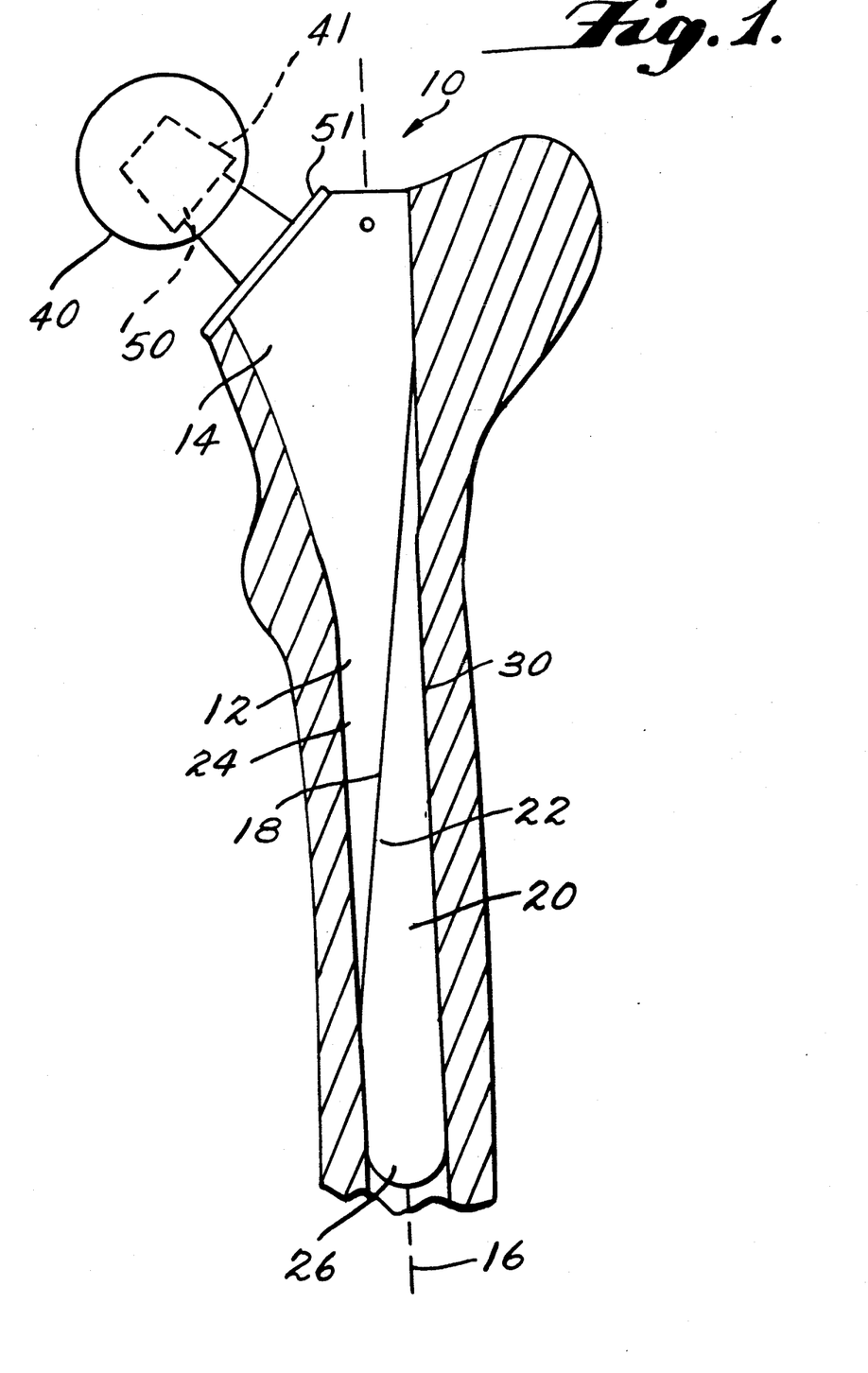
FIG. 1 is a side view in elevation of the device of the present invention.

Referring now to the drawings wherein like numerals designate corresponding parts throughout the several views, there is shown in FIG. 1 an anchoring device 10 of the present invention which, in the illustrated embodiment, is in the form of a hip joint prosthesis. It will be understood that the anchoring device 10 of the present invention may be employed in other surgical procedures which require the anchoring of a device to bone structure.

In the illustrated embodiment, the device 10 is inserted within a femoral canal 30. The ball shaped portion 40 is of a size to be carried within the natural or prosthetic acetabular cavity. As is conventional, the ball portion 40 is provided with a bore 41 for receiving a pin which is preferably in the form of a tapered neck and which extends transversely from a shoulder 5 of the device 10.

The body of the device 10 includes a first member 12 having an enlarged end 14 for the purpose of providing structural support for the neck 50 which is formed to extend at a angle to the axis 16 of the device 10. The member 12 opposite its end 14 has an abutment surface 18 which extends at an angle to the axis 16 of the device 10. The second member 20 of the device is provided with a surface 22 complementary to surface 18. The exterior configuration of the end portion 24 of member 12 and member 20 along approximately two thirds of the axis 16 remote from the end 14 will define a substantially cylindrical shaft body when in the assembled position illustrated in FIG. 1. The distal end 26 of the member 20 may be either smoothly rounded, as illustrated, or pointed to facilitate insertion into the femoral cavity.

Figures 2, 3A, 3B:
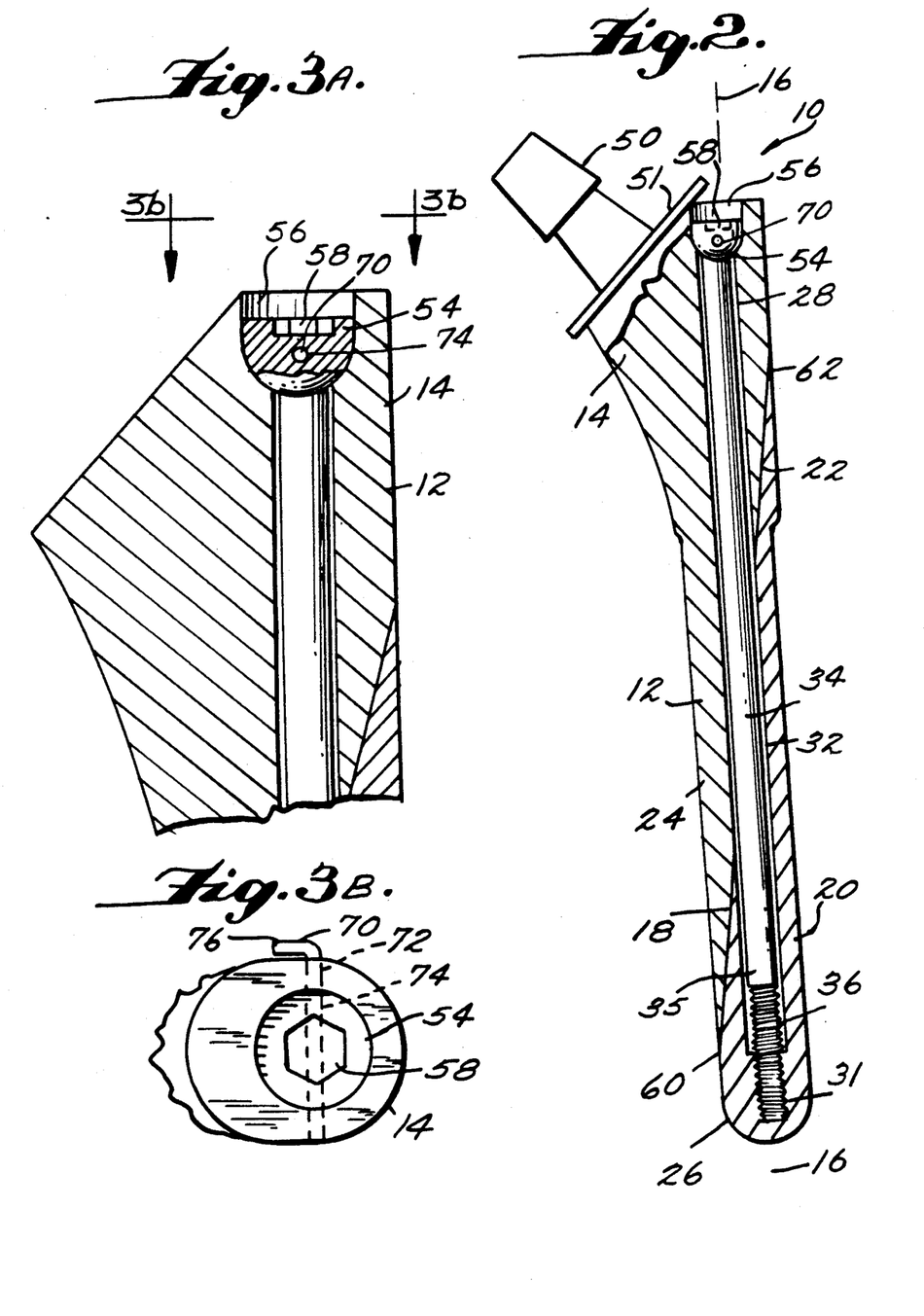
FIG. 2 is a sectional view along lines 2—2 of FIG. 1.
FIG. 3A is an enlarged detail view of the locking member of the device of the present invention and FIG. 3B is a view along lines 3b—3b of FIG. 3A.

With reference now to FIG. 2, there is shown a sectional view of the device 10 of FIG. 1 looking transverse to the axis 16. Member 12 has an internally formed through bore 28 which opens onto slide surface 18 in an elongated manner due to the angular interception of the surface 18 with the bore 28. Similarly, member 20 is provided internally with a bore 32 which opens onto face 22 in the same manner. Together the bores 28 and 32 form an internal cavity through which extends manipulating means in the form of a locking shaft 34 which at its end 35 is provided with a reduced diameter threaded extension 36 which is received in a threaded bore 31 in member 20. The opposite end of the shaft 34 is provided with an enlarged head 54 having a hemispherically shaped peripheral surface or wall and which is received in a bore 56, the inner end of which is also hemispherically shaped to complement the surface of the head 54 for reasons which will be discussed below. The exposed end of the head 54 is provided with a tool receiving recess 58 which may be hexagonal to facilitate cooperation with a mating tool to effect rotation of the shaft 34.

In use, once the receiving cavity in the femur has been prepared, the practitioner will insert the device 10 with the members 12 and 20 positioned so that the device will exhibit the minimum peripheral circumference. Typically, the cavity will have been prepared by drilling to the appropriate depth and diameter. In using the device 10 of this invention, it is preferable that the diameter of the femoral cavity be enlarged to a size only slightly larger than the minimum diameter of the assembled device 10 so as to permit manual insertion by the practitioner.

Once a device 10 is properly positioned, the user will then rotate the shaft 34 by insertion and rotation of the appropriate tool into recess 58. By rotation of the shaft 34 in one direction, the threaded interconnection between the extension 36 of shaft 34 and bore 31 will effect movement of member 20 toward end 14 of the device 10 thereby effecting a substantially uniform radial expansion of the device 10 between the points 60 and 62 along axis 16. Preferably, and depending on the precision of the drilling operation, the expansion required to effect secure anchoring will only be on the order of several millimeters or up to about 10 millimeters. In such circumstances, the material of the shaft 34 should normally be sufficiently resilient to easily tolerate the deflection caused by the relative sliding movement along surfaces 18 and 22 of members 12 and 20.

In some circumstances, particularly where larger relative motion between members 12 and 20 is required, the present invention will readily accommodate the deflection of the shaft 34 by the provision of the spherical interface between the head 54 and the lower end of bore 56. To this end, the interior diameter of the bores 28 and 32 are selected to provide a sufficient space between the internal surfaces of the bores 28 and 32 and the exterior diameter of the shaft 34. With this arrangement, as the member 20 moves upwardly as viewed in FIG. 2, the shaft 34 is free to pivot from its spherical head 54 to the desired extent to relieve any stress that normally would result from the relative movement of members 12 and 20.

With reference to FIGS. 3A and 3B, subsequent to the foregoing operation, further rotation of the shaft 34 may be prevented by the insertion of a locking pin 70 through a bore 72 provided adjacent the end 14 with the pin extending into an opening 74 formed in the head 54. A plurality of such openings 74 may be provided circumferentially spaced about the head 54 to accommodate various angular positions of the head 54 relative to the bore 72. The pin 70 may be bent at 76 to hold it in place and it will apparent to those skilled in this art that other devices for locking the shaft 34 in place may be employed.

From the foregoing, it will be apparent that adjustment as well as repositioning of the device 10 can be readily accomplished simply by unlocking the head 54 and reverse rotation thereof to effect reduction in the external circumference of the assembled members 12 and 20.

Figures 4, 5, 6:
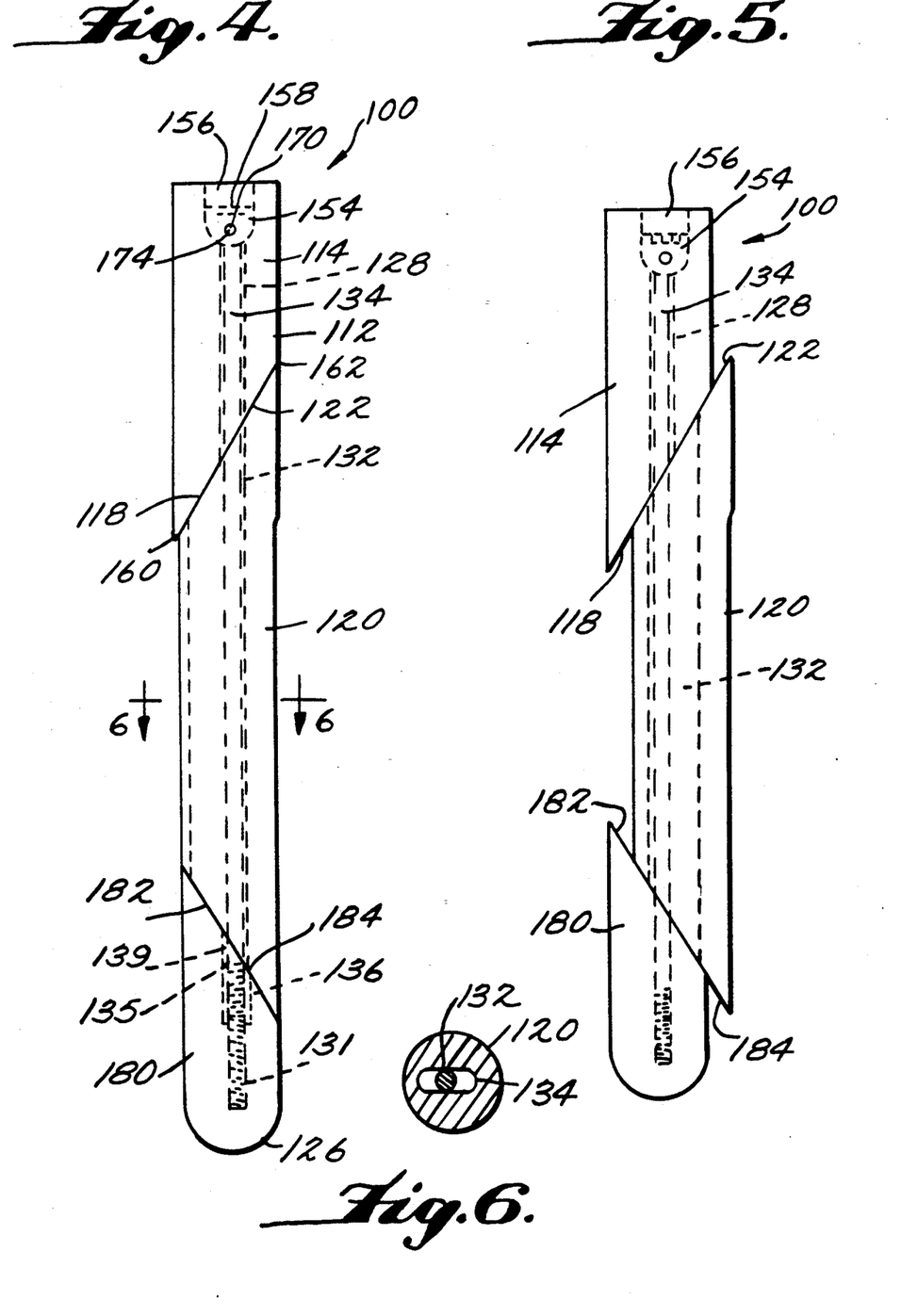
FIG. 4 is a side view in elevation of another embodiment of the invention.
FIG. 5 is a view similar to FIG. 4 but showing the members in their relative positions after expansion.
FIG. 6 is a view along lines 6—6 of FIG. 4.

With reference now to FIGS. 4–6, there is shown another embodiment 100 of the present invention where corresponding parts are referred to using numerals corresponding to the previous embodiment but raised by 100.

As shown in FIG. 4, the device 100 includes three members 114, 120 and 180. As will be apparent, the structure and operation of members 114 and 120 will be the same as described above in connection with the embodiment of FIGS. 1–3B. It will be noted, however, that sliding surfaces 118 and 122 intersect bores 128 and 132 at selected angles. Intermediate member 120 is provided with a bore 132 of increased width dimension as shown in FIG. 6 for reasons to be described below.

The intermediate member 120 is provided with a sliding surface 184 to complement a sliding surface 182 provided on the proximal end of the member 180. Also, the distal member 180 is provided with the threaded bore 131 in which is received the threaded end 136 of shaft 134 which extends entirely through the bore 132 of intermediate member 120. Lastly, it will be noted that the sliding surfaces 182 and 184 intercept their respective bores 132 and 139 at the same angle as surfaces 128 and 122 intercept bores 132 and 128 but rotated so as to extend in a complementary manner to surfaces 118 and 122. It will be apparent that the angles of interception may be different where it is useful to achieve relatively different expansion rates and which may impose correspondingly different forces. For example, in some patients, a portion of the femoral cavity may be substantially wider proximally than distally. In such a case, it will be useful to form the angle of interception of the surfaces 118 and 122 with the bores 128 and 132 with a much greater angle than the angle of interception of the surfaces 182 and 18 with their corresponding bores. With this modification, for a selected rotation of the shaft 134, member 112 will move laterally a greater distance than member 180. This will minimize or even eliminate the tendency of the device 100 to pivot in the femoral cavity about a site near the ball member where the device 100 is used in a hip prothesis.

Operation of the shaft 134 by rotation of head 154 is the same as in the previous embodiment except, with the structure of the embodiment of FIGS. 4–6, movement of the distal member 180 upon rotation of the shaft 134 will effect movement of the intermediate member 120 as a result of shifting of member 180 along the axis of shaft 134 towards member 114. Locking of the members in the position as illustrated in FIG. 5 is effected also in the same manner as in the previous embodiment.

By making the bore 132 of the intermediate member 12 of greater width, as shown in FIG. 6, a substantially greater latitude in radial expansion of the device 100 can be achieved. In addition, axial misalignment of a bone cavity can be tolerated as the degree to which the shaft 134 is deflectable is increased. The shaft, when the device is in the locked condition, in a cavity, will normally not be a load bearing member as the loads will be transmitted substantially through the surfaces 118, 122, 182 and 184 and the associated members 114, 120 and 180.

Figure 7:
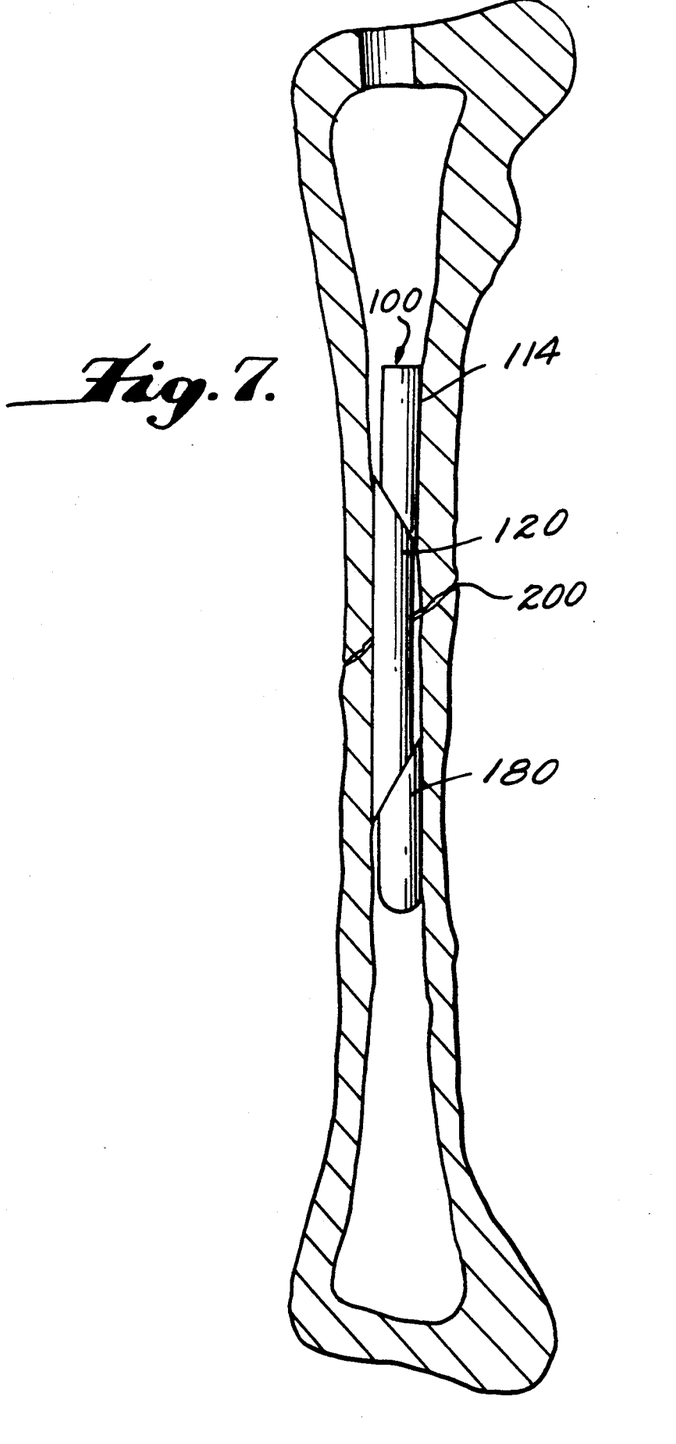
FIG. 7 is a view of the locking device of FIGS. 4-6 in one example of use.

The embodiment 100 of the present invention is particularly useful in securing together pieces of a broken bone particularly where the break is a spiral fracture or comminuted fracture. In these types of fractures, the device 100 would be used by insertion in the bone cavity to an extent to traverse the fracture as shown in FIG. 7 where the device 100 is installed so as to straddle the site of a break 200. Also as shown, the intermediate member 120' may be slightly curved to facilitate placement of the device about the break and allows more secure locking of the device in place. The practitioner would then secure the device 100 in place by effecting the relative shifting of the members, as described above, but with an extended length tool to thereby immobilize the fracture fragments in the desired position. In insertion of the device 100, the ability of the member 180 to shift laterally relative to the member 114 will also allow the device to compensate for the natural curvature of the bone cavity, where necessary.

Figure 8A:
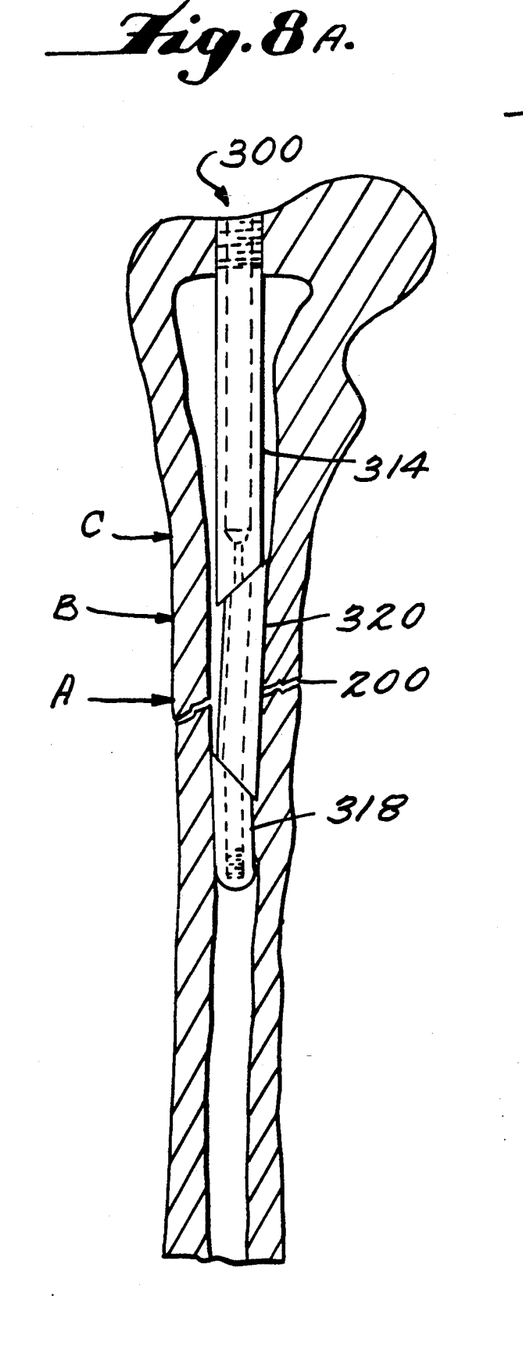
FIGS. 8A, 8B and 8C are side views of another embodiment of the present invention.
Figure 8B:
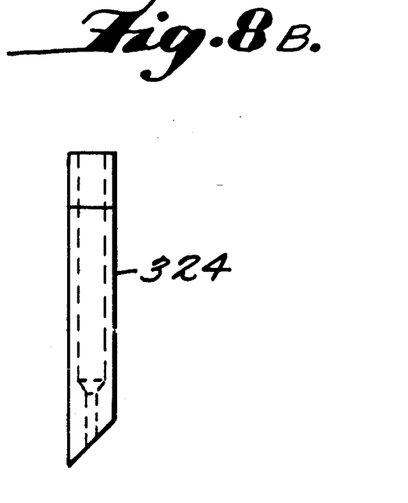
Figure 8C:
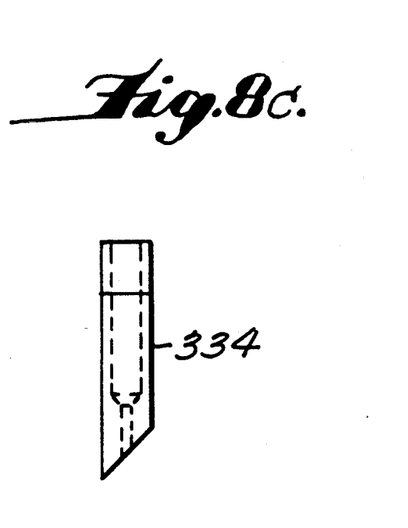

With reference to FIGS. 8A-8C, another embodiment 300 of the present invention is shown.

As shown in FIG. 8A, the device 300 includes three members 314, 320, and 318, which expand in an identical manner as described above with reference to FIGS. 4–7. However, unlike device 100 as shown in FIG. 7, the member 314 of the device 300 extends from an opening in the bone cavity to the intermediate member 320. An end portion 314 is positioned in the opening (which was drilled to permit insertion of the device 300) and has threads 312 to mate with an extraction tool (not shown). Accordingly, the extension member 314 permits the practitioner to adjust the device 300 to the desired expanded diameter from the end portion 316 and to easily remove the device 300 after the bone has mended.

The extension member 314 is of relatively long length and thus, is employed to position properly the members 320 and 318 in relation to the break site 200 located at position A.

FIGS. 8B and 8C illustrate extension members having lengths differing from the extension member 314 shown in FIG. 8A. In FIG. 8B, the extension member 324 is of intermediate length. Thus, if the break site 200 were located at position B on the bone (see FIG. 8A), the intermediate extension member 324 would be employed to position properly the center of the member 320 at the break site 200.

In FIG. 8C, the extension member 334 is relatively short in length. Thus, if the break site 200 were located at position C on the bone, the short extension member 334 would be employed.

As may be appreciated from the three different extension members 314, 324, 334 in FIGS. 8A-8C, the extension member may be designed to any length appropriate to position members 318 and 320 properly at any break site.

Figures 9, 10:
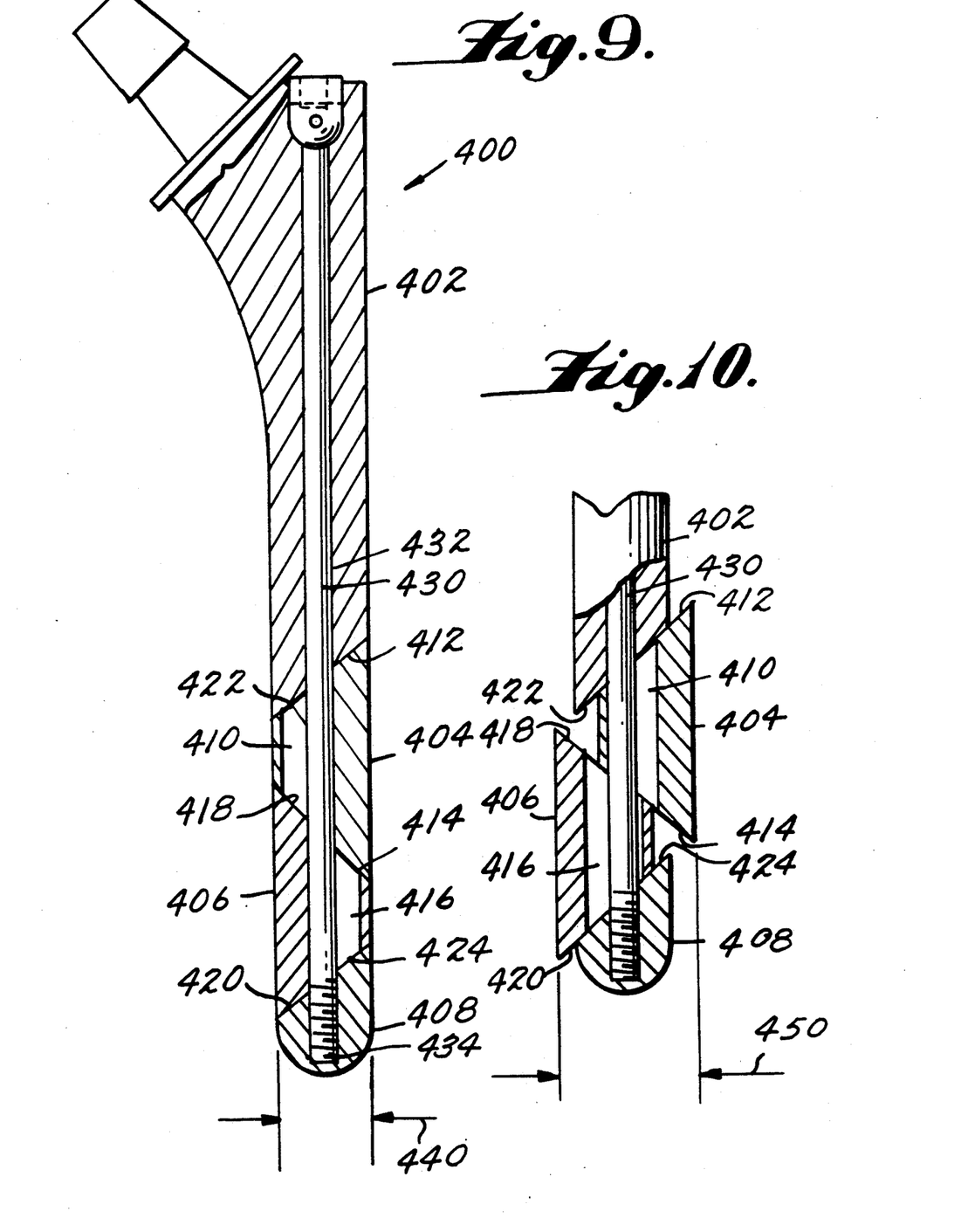
FIG. 9 is a view of yet another embodiment of the present invention.
FIG. 10 is a view similar to FIG. 9 but showing the members in their relative positions after expansion.

With reference now to FIG. 9, device 400 includes four members 402, 404, 406 and 408, the structure and operation of which are the same as described in FIGS. 4–7. However, unlike the embodiment shown in FIGS. 4–7, the device 400 has two intermediate members 404 and 406. Intermediate member 404 is provided with a bore 410 of increased width dimension (same as shown in FIG. 6), and two sliding surfaces 412 and 414, which intersect bore 410 at selected angles. Similarly, intermediate member 406 is provided with a bore 416 of increased width dimension (similar to shown in FIG. 6), and two sliding surfaces 418 and 420, which intersect bore 416 at selected angles. As with the embodiments described above, the angles of interception may be different according to desired expansion rates.

The proximal member 402 and the distal member 408 are also provided with sliding surfaces 422 and 424, respectfully. Each sliding surface on the members 402, 404, 406 and 408 complements the adjacent sliding surface. For example, sliding surface 422 of member 402 complements sliding surface 412 of intermediate member 404.

The proximal member 402 is provided with bore 432 having a diameter slightly larger than that of shaft 430, thereby permitting the shaft 430 to rotate, yet preventing the shaft 430 from displacing laterally. The upper portions of proximal member 402 and shaft 430 are identical to that shown in FIG. 2.

The distal member 408 is provided with bore 434, which has threads to mate with threads provided at the distal end of the shaft 430.

The shaft 430 extends entirely through bores 410 and 416 of respective intermediate members 404 and 406 and is inserted into threaded bore 432 of distal member 408. Upon rotation of shaft 430, both intermediate members 404 and 406 are displaced outwardly from the shaft 430 as shown in FIG. 10. According to this embodiment, the expansion device 400 has a diameter 450 which may be approximately 33% greater than the diameter 440 of the unexpanded device 400 of FIG. 9, although smaller expansions may be effected if desired.

Figure 11:
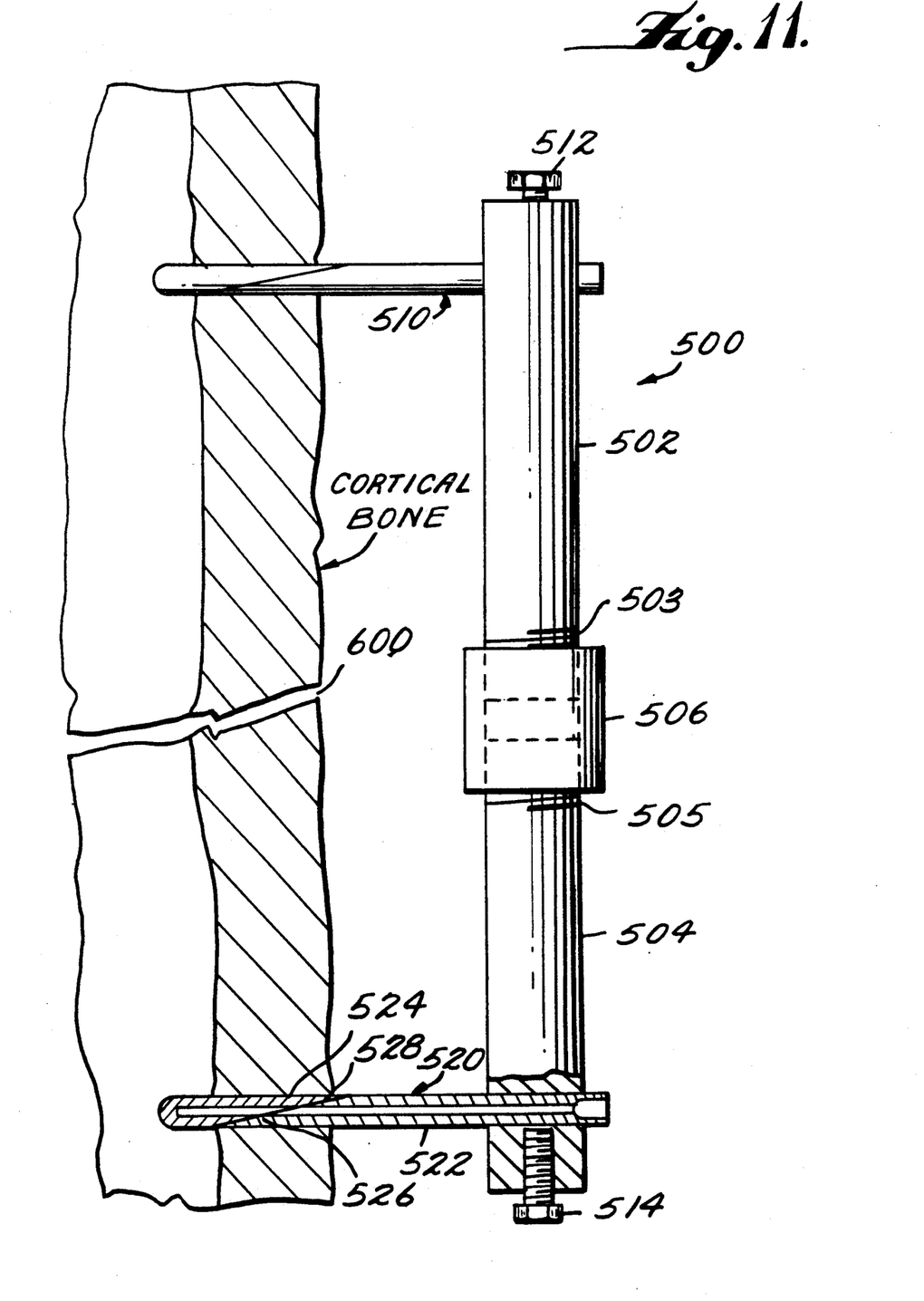
FIG. 11 is a view of another embodiment of the present invention.

As shown in FIG. 11, device 500 is a non-invasive type system and includes two mounting brackets 502 and 504 having respective threaded end portions 503 and 505, linked by a threaded turnbuckle 506. A expandable shaft 510 is positioned at the end of mounting bracket 50 opposite the threaded portions 503 and secured to the bracket 502 by locking bolt 512. Likewise, an expandable shaft 520 is positioned at the end of mounting bracket 504 opposite the threaded portions 505 and secured to the bracket 504 by locking bolt 514.

The shafts 510 and 520 operate in the same manner as the structure described with reference to FIG. 2. For example, the shaft 520 has two members 522 and 524 which may be moved relatively along sliding surfaces 526 and 528, thereby expanding the diameter of the shaft 520.

In operation, the shafts 510 and 520 are inserted into previously drilled holes in the bone located on opposite sides of the break site 600. The shafts 510 and 520 are then expanded to anchor them in the holes formed in the bone. The mounting members 502 and 504 are secured via locking bolts 512 and 514 to the shafts 510 and 520. The turnbuckle 506 is then rotated to draw the mounting members 502 and 504 toward each other, thereby applying through the shafts 510, 520 binding pressure to the break site.

With reference now to FIGS. 12A-12C and 13, device 600 includes two members 602 and 604. The general structure and operation of device 600 is the same as described in FIGS. 2-3. However, members 602 and 604 have a dove-tail joint arrangement which prevents relative rotation about the axis of the device and between the members 602 and 604 during the expansion of the device 600.

Distal member 604 has two dove-tail shaped tabs 610 and 62 protruding from a sliding surface 606. As best shown in FIG. 12B, the tabs 610 and 620 are linearly aligned on opposite sides of bore 608. Each tab 610 and 620 has a narrow lower portion 612 and 622 which widens to a wide upper portion 614 and 624, respectively. Hence, each tab 610 and 620, when viewed cross-sectionally to the linear alignment, is trapezoidal or "dove-tail" shaped.

Proximal member 602 has two complimentary, dove-tail shaped slots 630 and 640 formed in a sliding surface 626. As shown in FIG. 12C, the slots 630 and 640 are linearly aligned on opposite sides of bore 628. Each slot 630 and 640 has a narrow portion 632 and 642 along the sliding surface 626 which widens inwardly from the sliding surface 626 to a wide portion 682 and 692, respectively. The dimensions of slots 630 and 640 are designed to communicate with the tabs 610 and 620 such that tabs 610 and 620 may slide smoothly therein.

According to this embodiment, when the shaft 634 shown in FIG. 13 and of the same structure as the embodiment shown in FIGS. 2-3) is rotated to expand device 600, the communication of tabs 610 and 620 of distal member 604 and the slots 630 and 640 of proximal member 602 prevents any relative radial rotation between members 602 and 604 during the movement of sliding surfaces 626 and 606.

Figure 12A:
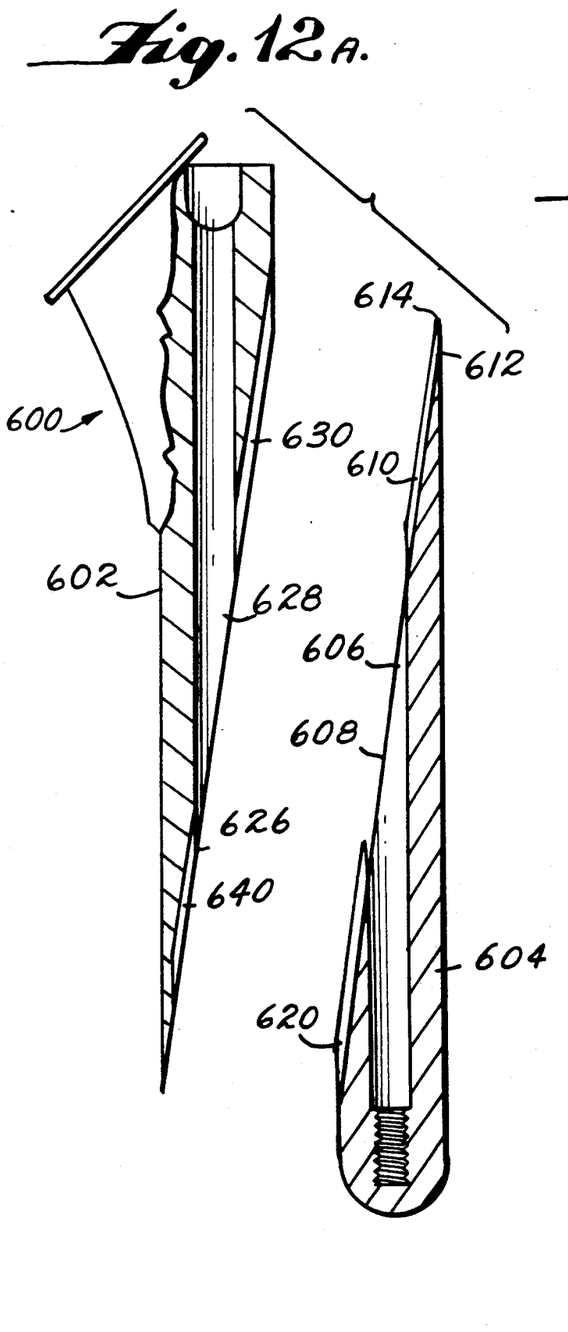
FIG. 12A is an unassembled side view of another embodiment of the present invention.
Figure 12B:
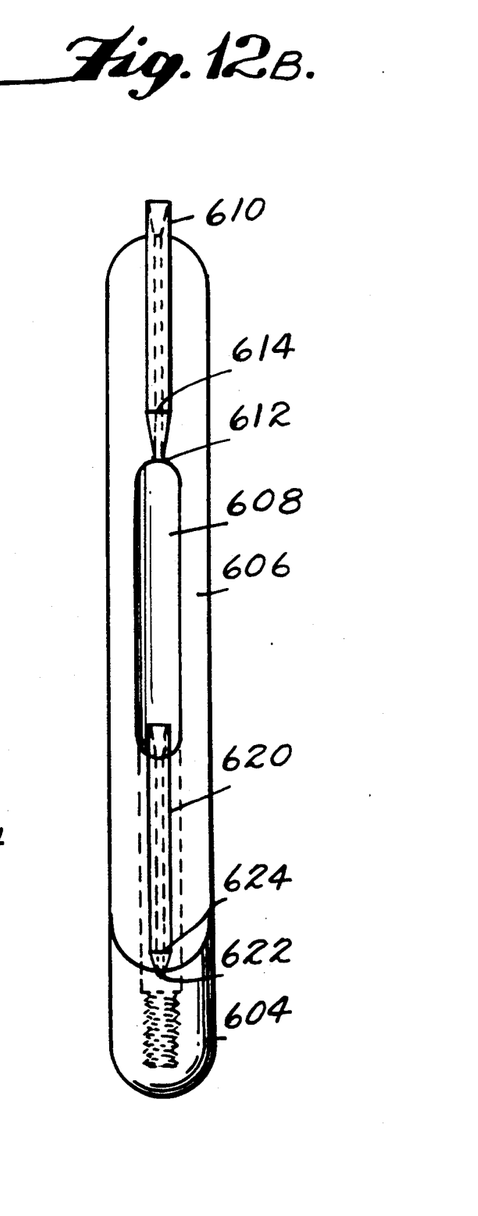
FIG. 12B is a front view of the distal member of the embodiment shown in FIG. 12A.
Figures 12C, 13:
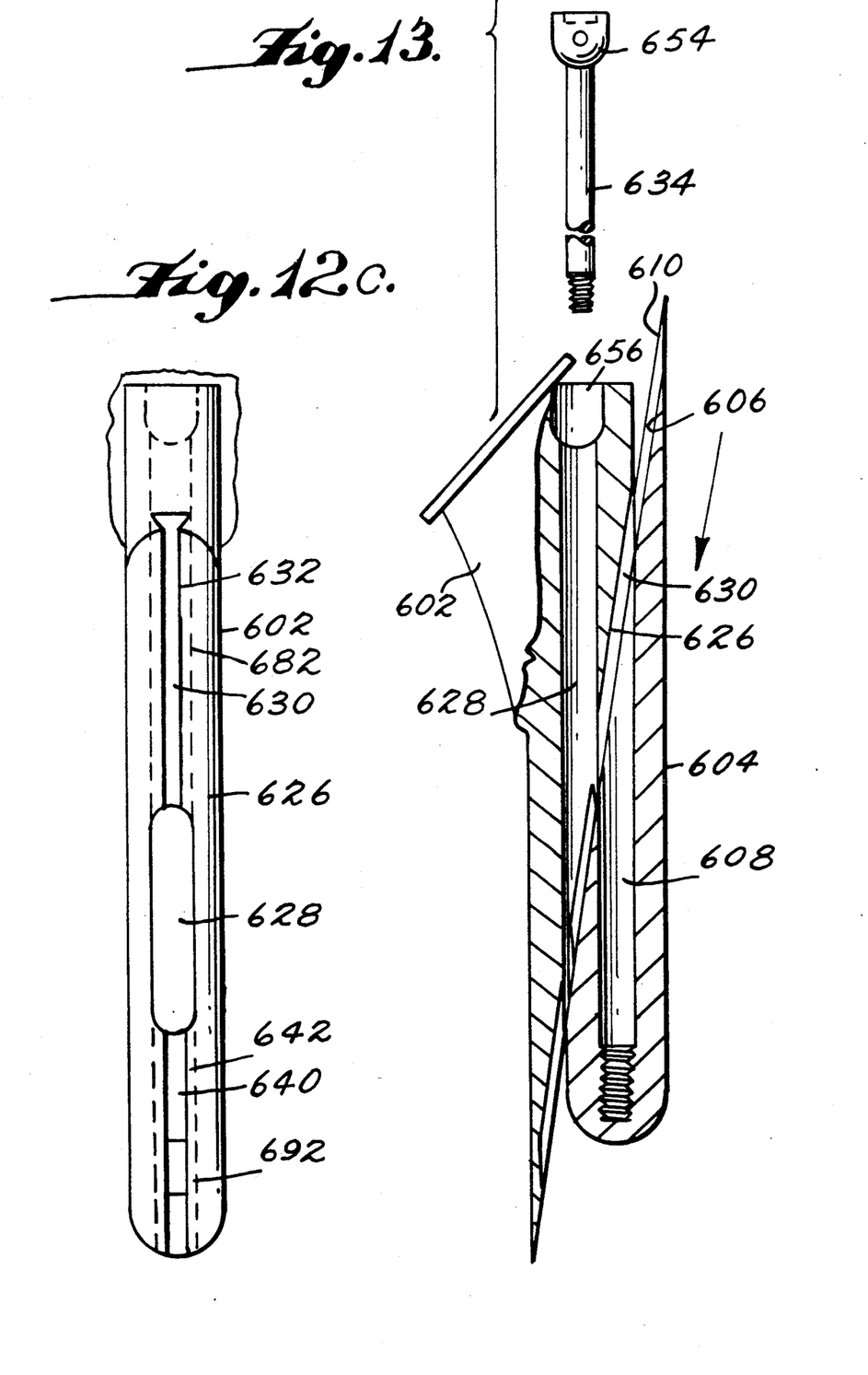
FIG. 12C is a rear view of the proximal member of the embodiment shown in FIG. 12A.
FIG. 13 is side view in section showing assembly of the device.

Although two sets of dove-tail joints are shown in FIGS. 12A-12C, a single dove-tail joint located on one side of the bore may be employed to prevent rotation. Further, the dove-tail arrangement described for the two member embodiment may also be employed in the three member devices of FIGS. 4-8, the four member devices of FIGS. 9-10, and the expansion shafts of the device shown in FIG. 11 between any pair of adjacent members.

It will also be apparent to those skilled in this art that the device of the present invention may be employed to effect other types of surgical procedures where it is desired, for example, to join broken diseased or deformed bones or portions thereof by the use of a structure of the present invention having different overall relative dimensions compared to that which would be employed in the illustrated embodiments.

Having described the invention, it will be apparent that various other modifications may be made thereto without departing from the spirit and scope of this invention as defined in the appended claims.

What is claimed is:

1. A prosthetic positioning device adapted for cooperation with an interior surface of a bone cavity, the positioning device comprising separation first, second and third elongated members, said first member having an elongated bore extending therethrough from one end of said first member to an opposite end, said second member having an elongated bore extending therethrough from one end of said second member to at least adjacent an opposite end, said opposite end of said first member and said one end of said second member being disposed to face each other with facing end surfaces extending at acute angles to said respective bores to form a first slide surface with said extending angles being substantially equal, said third member having an elongated bore extending therethrough from one end of said third member to an opposite end, said opposite end of said second member and said one end of said third member being disposed to face each other with facing end surfaces extending at acute angles to said respective bores to form a second slide surface with said extending angles being substantially equal, said positioning device further including an elongated actuatable manipulation means configured to be disposed within said bores of said first, second, and third members for holding said first and second slide surfaces in abutting relation to one another and, upon actuation of said manipulation means, causing relative sliding motion along said first and second slide surfaces thereby varying at least the width dimension of said positioning device.

2. A prosthetic positioning device for cooperation with the interior surface of a bone cavity, the positioning device comprising a first elongated member having a bore extending therethrough from one end of said first member to an opposite end, a second elongated member having a bore formed therethrough extending through the length of said second member from one end to an opposite end, said opposite end of said first member and said one end of said second member being disposed to face each other with facing end surfaces extending at acute angles to said respective bores to form a first slide surface with said extending angles being substantially equal, a third member having a bore extending therethrough from one end of said third member to an opposite end, said opposite end of said second member and said one end of said third member being disposed to face each other with facing end surfaces extending at acute angles to said respective bores to form a second slide surfaces with said extending angles being substantially equal, a fourth member having a bore extending therethrough from one end of said fourth member to at least adjacent an opposite end, with said opposite end of said third member and said one end of said fourth member being disposed to face each other with facing end surfaces extending at acute angles to said respective bores to form a third slide surface with said extending angles being substantially equal, said positioning device further including an elongated actuatable manipulation means configured to be disposed within said bores of said first, second, third, and fourth members for holding said first, second, and third slide surfaces in abutting relation to one another and, upon actuation of said manipulation means, causing relative sliding motion amongst said first, second, third, and fourth members along said slide surfaces to thereby vary at least the width dimension of said positioning device.

3. A prosthetic positioning device for cooperation with the interior surface of a bone cavity, the positioning device comprising a first elongated member having a bore extending therethrough from one end of said first member to an opposite end, a second elongated member having a bore extending therethrough from one end of said second member to at least adjacent an opposite end, said opposite of said first member and said one end of said second member being disposed to face each other with facing end surfaces extending at acute angles to said respective bores to form a slide surface with said extending angles being substantially equal, said angled surface of said opposite end of said first member having a slot formed therein, said slot lying on a line along the direction of said sliding motion, said angled further of said one end of said second member having a projection thereon, said projection also lying on a line along the direction of said sliding motion, said projection and said slot being so shaped and so positioned as to interengage with one another such that said angled surfaces abut one another when said projection is disposed in said slot, said positioning device further including manipulation means configured to be disposed within said bores of said first and said second members for holding said slide surface in abutting relation and, upon actuation of said manipulation means, causing relative sliding motion among said first and said second members along said slide surfaces to thereby vary at least the width dimension of said positioning device.

4. A method of treating a break or fracture at a site on a bone having an interior cavity with a device of the type including a plurality of first elongated members of varying lengths, each said first elongated member having a bore extending therethrough from one end of each said first member to an opposite end, a second elongated member having an elongated bore extending therethrough from one end of said second member to an opposite end, said opposite end of said first member and said one end of said second member being disposed to face each other with facing end surfaces extending at acute angles to said respective bores to form a first slide surface with said extending angles being substantially equal, a third elongated member having an elongated bore extending therethrough from one end of said third member to at least adjacent an opposite end, said opposite end of said second member and said one end of said third member being disposed to face each other with facing end surfaces extending at acute angles to said respective bores to form a second slide surface with said extending angles being substantially equal, said positioning device further including an elongated actuatable manipulation means configured to be disposed within said bores of said first, second, and third members for holding said first and said second slide surfaces in abutting relation to one another and, upon actuation of said manipulation means, causing relative sliding motion amongst said first, second, and third members along slide surfaces to thereby vary at least the width dimension of said positioning device, the steps including (a) opening the bone cavity, (b) removing the tissue contained in the bone cavity, (c) selecting one of said plurality of said first members, said selection being dependent upon the location of said site of break or fracture with the required length of said first member being directly proportional to the distance between said site of break or fracture and the cavity opening, (d) inserting said selected first member and said second and said third members into said cavity to such a depth that at least one of said second and said third members extends along said site of break or fracture and said one end of said first member is positioned in the cavity opening, (e) actuating said manipulation means to cause said relative sliding motion to increase the width dimension of said device to thereby secure the device against the interior surface of the bone cavity so as to hold said site of break or fracture in a fixed and stable position relative to said device.

5. A method of treating a break or fracture at a site on a bone having an interior cavity with a device of the type including a first elongated member have a bore extending therethrough from one end to an opposite end, a second elongated member having an elongated bore extending completely therethrough from one end to an opposite end, said opposite end of said first member and said one end of said second member being disposed to face each other and having end surfaces extending at acute angles to said respective bores to form a first slide surface with said extending angles being substantially equal, a third elongated member having an elongated bore extending completely therethrough from one end to an opposite end, said opposite end of said second member and said one end of said third member being disposed to face each other and having end surfaces extending at acute angles to said respective bores to form a second slide surface with said extending angles being substantially equal, a fourth member having a bore extending from one end to at least adjacent an opposite end, said opposite end of said third member and said one end of said fourth member being disposed to face each other end having end surfaces extending at acute angles to said respective bores to form a third slide surface with said extending angles being substantially equal, said positioning device further including an elongated actuatable manipulation means configured within said bores for holding said first, second, and third slide surfaces in abutting relation to one another and upon actuation of said manipulation means, causing relative sliding motion between said first, second, third, and fourth members along said slide surfaces to thereby vary at least the width dimension of said positioning device, the steps comprising opening the cavity of the bone, removing tissue from the cavity, inserting said device into said cavity to such a depth that at least one of said second and third members extends along said site of break or fracture, actuating said manipulation means to cause relative sliding motion to increase the width dimension of said device to thereby hold said site of break or fracture in a fixed an stable position relative to said device.

6. The prosthetic positioning device as claimed in claim 1 further comprising means for preventing relative rotation between at least one adjacent pair of said members during actuation of said manipulation means.

7. The prosthetic positioning device as claimed in claim 2 wherein said opposite end of said fourth member is closed and said bore of said forth member adjacent to said closed end is formed with a threaded portion and said manipulation means comprising a shaft having a diameter less than the diameter of said bores of said first, second, third, and fourth members, said shaft having a threaded end engaged in said threaded portion of said fourth member whereby rotation of said shaft in one direction will cause said sliding motion amongst said first, second, third and fourth members along said slide surfaces to increase the width dimension of said device in the area where said slide surfaces overlap said shaft and rotation of said shaft in a direction opposite said one direction will cause said sliding motion to decrease said width dimension.

8. The invention as claimed in claim 2 wherein said manipulation means is a shaft configured within said bores of said members with said shaft being engaged by said threaded end with said bore of said fourth member so that rotation of said shaft will cause said sliding motion.

9. The invention as claimed in claim 7 wherein said bore of said first member at said one end of said first member is formed with a counter-bore at least a portion of which has a diameter larger than the diameter of said bore of said first member, said shaft having a head portion received in said counter-bore.

10. The invention as claimed in claim 9 wherein said counter-bore has a curved inner wall surrounding said bore of said first member and said head portion of said shaft has a curved surface surrounding said shaft and mating with said curved inner wall of said counter-bore, said bores of said members having a width dimension greater than the diameter of said shaft so that, upon occurrence of said sliding motion, said shaft is pivotable on said head portion.

11. The invention as claimed in claim 9 wherein said head portion has recess means for cooperation with tool means for rotating said head portion and shaft.

12. The invention as claimed in claim 6 wherein said one end of said first member and said head portion have removable, interengageable locking means for preventing rotation of said shaft.

13. The invention as claimed in claim 7 wherein the cross-section of said bores of said second and said third members taken perpendicularly to the axes of said second and said third members is oval in shape, thereby permitting said second and said third members to move perpendicularly to said axes over said shaft.

14. The invention as claimed in claim 2 further comprising means for preventing relative rotation between at least one adjacent pair of said members during actuation of said manipulation means.

15. The prosthetic positioning device as claimed in claims 6 or 14 wherein said rotation prevention means further comprises at least one projection protruding from a slide surface of one of the adjacent members and at least one slot formed in a slide surface of the other of the adjacent members, wherein said projection interengages with said slot such that said projection slides within said slot during the actuation of said manipulation means and said projection and slot interengagement prevents said adjacent members from rotating relative to each other during the actuation.

16. The method as claimed in claim 5 including the step locking said manipulation means to fix the position of said manipulation means subsequent to said actuating step.

* * * * *